Figure 1:
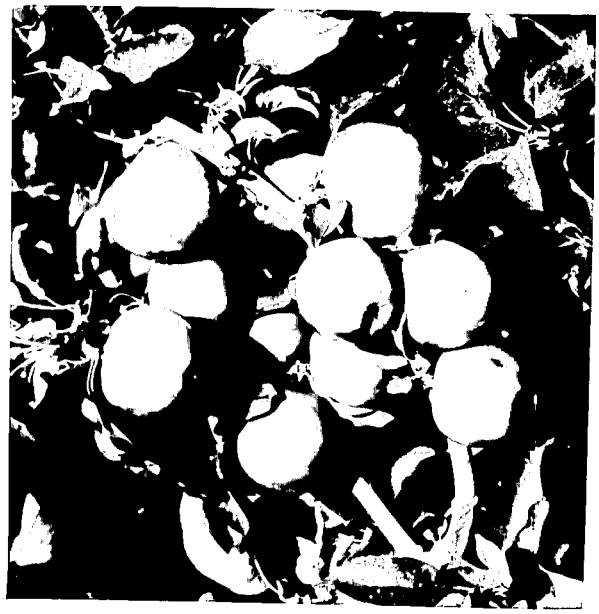

United States Patent [19]

Cooper

[11] Patent Number: Plant 5,761

[45] Date of Patent: Jul. 8, 1986

[54] APPLE TREE EARLEE GRANNEE STRAIN

[76] Inventor: Calvin L. Cooper, Rte. 1, Brewster, Wash. 98812

[21] Appl. No.: 667,555

[22] Filed: Nov. 2, 1984

[51] Int. Cl.[4] ..... A01H 5/00

[52] U.S. Cl. ..... Plt./34

[58] Field of Search ..... Plt./34

[56] References Cited

U.S. PATENT DOCUMENTS

| | | | |
|---|---|---|---|
| P.P. 3,453 | 1/1974 | Hannaford | Plt./34 |
| P.P. 4,676 | 3/1981 | Cooper | Plt./34 |
| P.P. 4,741 | 6/1981 | Cooper | Plt./34 |

*Primary Examiner*—James R. Feyrer

*Attorney, Agent, or Firm*—Eugene D. Farley

[57] ABSTRACT

The presently described apple tree originated as a genetic bud sport on a Summerland strain of non-spur, unpatented, Granny Smith apple tree in the Calvin L. Cooper orchard located near Brewster, Wash. The new variety of apple tree is somewhat more compact in structure than is its parent, but otherwise is generally similar to the latter with respect to trunk, branches, leaves and flowers. However, its fruit is uniquely characterized by its property of maturing early, i.e. up to 14 days earlier than the fruit of its parent regular Granny Smith variety. This property is evidenced by early loss of the characteristic white spots from its skin, and in particular by early and substantial rise in soluble solids content and early, rapid, and substantial drop in total acidity. It also is noticeably lighter in color.

4 Drawing Figures

The present invention relates to a new and distinct variety of apple tree, specifically to the Early Granny variety, now, by change of name, denominated the EarleeGrannee variety.

I discovered my new variety of apple tree in my cultivated apple orchard located near Brewster, Wash. It was a member of a group of trees comprising cuttings of the Summerland (regular) strain of non-spurred Granny Smith apple tree grafted in the year 1976 to Merton-Malling 111 (MM111) root stock.

As time went on, and specifically about the year 1979, I noticed that one of the trees of the group had decidedly unique characteristics. It was medium in size. The structure of the tree itself was more compact than the structure of its companion Granny Smith apple trees.

Its fruit was particularly unique. As it matured, the fruit became noticeably lighter in color. The white spots characteristic of the conventional Granny Smith apple disappeared to a greater extent. The flesh of the fruit became very white.

In particular, the eating qualities of the fruit improved at an early date. The fruit became sweeter in taste. Controlled tests indicated early maturing, as evidenced by early rise in total soluble solids and an early, rapid, and substantialdrop in total acidity. Maturation of the fruit occurred up to 14 days earlier than maturation of the fruit of the standard Granny Smith apple tree. In addition, the fruit harvest contained a noticeably increased proportion of dessert quality specimens.

During the years subsequent to 1979, I propagated bud wood from the parent tree onto suitable root stock and established that the noted characteristics of early maturing of the fruit persisted to the fourth generation.

In the year 1981, for example, I conducted tests comparing the soluble solids and acid content of my new "EarleeGrannee" apples with the same properties of standard Granny Smith apples. The apples tested were grown in the same or neighboring orchards and were picked and tested on the same day. The tests were carried out by USDA personnel in the USDA laboratories located at Wenatchee, Wash. The results are tabulated below:

| | Standard Granny Smith | | "EarleeGrannee" | | | |
|---|---|---|---|---|---|---|
| Date | Soluble Solids | Acid | Soluble Solids | Increase (%) | Acid | Decrease (%) |
| 8/31/81 | 9.2 | 1.022 | 10.2 | 11 | .811 | 21 |
| 9/7/81 | 8.7 | .985 | 10.7 | | .794 | |
| 9/14/81 | 9.6 | .922 | 11.2 | 14 | .771 | 16 |
| 9/21/81 | 9.8 | .924 | 11.2 | | .694 | |
| 9/28/81 | 11.8 | .841 | 11.8 | | .673 | |
| 10/12/81 | 11.0 | .771 | 11.6 | 5 | .652 | 15 |

The foregoing test results conclusively establish the early maturing and early development of desirable eating qualities in my hereindescribed new apple variety "EarleeGrannee".

A more detailed botanical description of my new apple tree variety and of its fruit follows. In this description, the color values recited are in accordance with the Nickerson Color Fan published by the American Horticultural Council, Arnold Arboretum, Jamaica Plains, Mass.

The description is made with particular reference to the drawings, wherein:

FIG. 1 is a photograph of a cluster of limbs of my new EarleeGrannee apple tree variety, illustrating the compactness of the tree and the clustering habit of the fruit which it bears.

Figure 2:
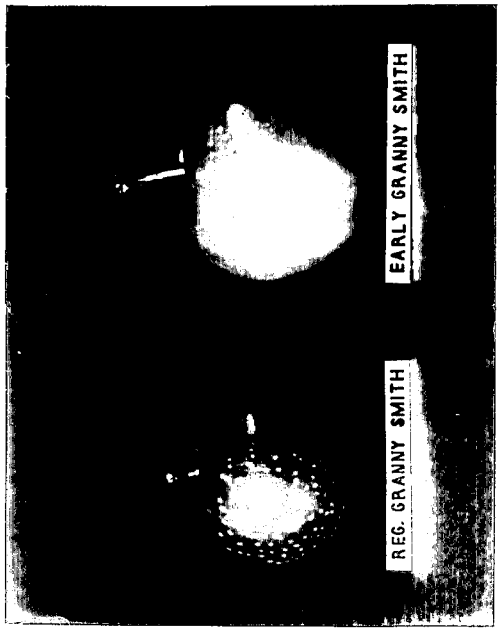

FIG. 2 is a photograph of one of the fruits of my new apple tree variety, labelled by its original name "Early Granny Smith". Also illustrated for purposes of comparison is the fruit of a standard or regular Granny Smith apple tree. The loss of skin spots and lightening of skin color upon maturing are evident. Both apples were grown in the same agricultural area, and both were picked on the same day.

Figure 3:
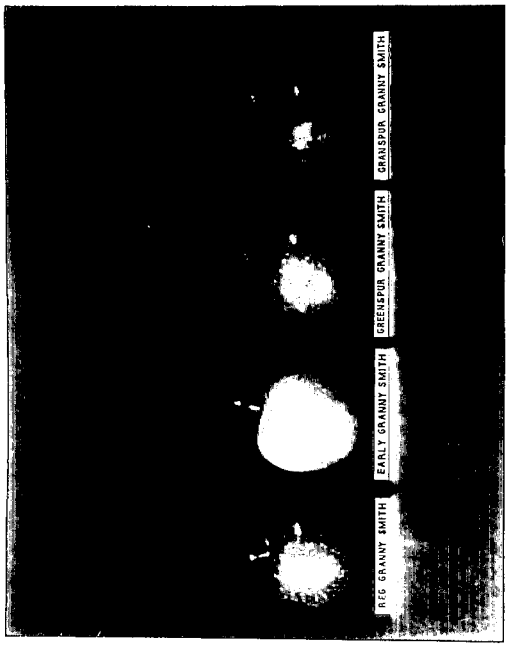

FIG. 3 is a photograph comparing the appearance of my new apple variety, designated by its original name of "Early Granny Smith", with the appearance of regular Granny Smith, and of two hybrid, spur-type, Granny Smith apple trees, i.e. the Greenspur Granny Smith and the Granspur Granny Smith. All four apples were grown in the same or adjacent orchards and were picked on the same day.

Figure 4:
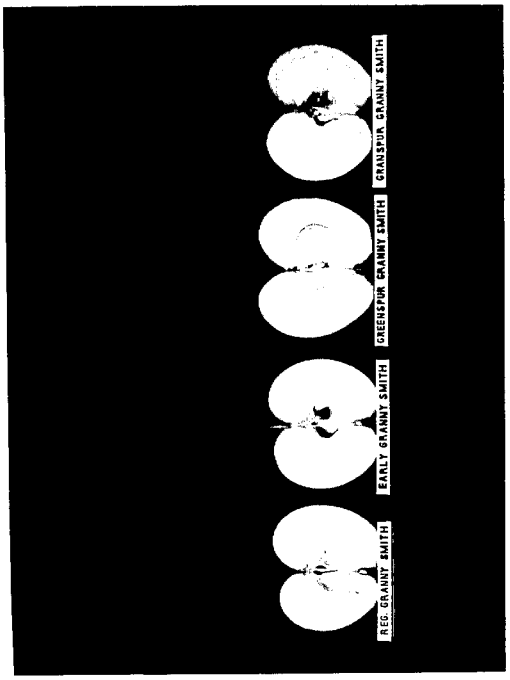

FIG. 4 is a photograph of specimen apples of the same varieties shown in FIG. 3, with the specimens cut in half. All specimens were grown in the same or adjacent orchards, and were picked on the same day. The early maturity of the hereindescribed "EarleeGrannee" (Early Granny Smith) apple is evident as shown by (1) the dark brown color of the seeds and (2) the whiteness of the flesh.

Parentage: Discovered as an early maturing, budded, whole tree from the "Summerland" strain of regular Granny Smith. Original tree was discovered from a 1976 graft on MM111 rootstock.

Date of fruit maturity: Matures 7–10 days earlier than standard Granny Smith. In Brewster, Wash., fruit was mature (Total Soluble Solids exceeded 11%) on Oct. 1 in 1982 and 1983.

Tree: Medium size, of moderate vigor with internodes slightly more compact than "Granspur" (U.S. Plant Pat. No. 4,676) and much more compact than regular Granny Smith (Average internodal length on 1-year old shoots=18 mm of EarleeGrannee vs 21 mm on Granspur and 28 mm on regular Granny Smith under Brewster, Wash., growing conditions). Tree is very precocious.

Trunk: Medium thick, spurs slightly closer together than "Granspur".

Leaves: Large, ovate point tapered, margin slightly serrated. Length 90 mm to 100 mm, width 65 mm to 70 mm, color, strong yellowish green (2.5G 5/9) petiole; long, medium thick, moderately pubescent.

Flowers: Color: Petals white to pale purple (7.5P 9/2), stigma and style light green (2.5GY 8/9), filament white, anther brilliant yellow green (2.5GY 9/8).

Bloom:

*First bloom.*—Apr. 23, 1983.

*Full bloom.*—Apr. 27, 1983.

Fruit: Maturity when described=Mature from tree (Oct. 4, 1983).

*Size.*—Medium, Equatorial diameter 75 mm to 90 mm.

*Form.*—Uniform, rounded to slightly oblate (L/D ratio 0.98).

*Cavity.*—Smooth, deep, conical, symmetrical. Depth 15 mm to 18 mm. Width 24 mm to 29 mm.

*Stem.*—Medium to heavy, flexible, strongly attached.

*Calyx.*—Sepals, pointed, prominent in a large basin, pubescent.

*Basin.*—Smooth, rounded shoulder, depth 12 mm to 15 mm. Width 28 mm to 32 mm.

*Skin.*—Smooth, glossy, medium thickness (slightly thinner than Standard Granny Smith). Dots (lenticles) small, white, evenly distributed over shoulders and main portion of the fruit but more numerous in basin. Color: brilliant yellow green (2.5GY 8/9) with a tendency for the exposed side of the fruit to form a brilliant greenish yellow blush (10Y 9/9). Flavor tends to be tart, but less so than fruit of regular Granny Smith.

*Flesh.*—White, crisp, very little green color at skin. Cut surface remains white, flavor sweet and mild.

*Core.*—Core line visible in cross-section, ovate seed cavities, vascular bundles inconspicuous, calyx closed, narrow, long; styles persistent.

*Stamen.*—Single whorl, persistent.

*Seeds.*—Number 4 to 7 at maturity. Length 6 mm to 7 mm, breadth 4 mm to 5 mm. Shape is acute, color is mixed shades of reddish brown (10YR 5/69).

Use: Fresh dessert, baking or processing.

Keeping quality: Shelf life good, 150 to 160 days in cold storage.

Unique characteristics of fruit: Fruit gains a high level of sweetness and the flesh loses its green color well ahead of "Granspur" or regular Granny Smith.

Comparison: Compared to "Granspur" or regular Granny Smith, the fruit matures earlier in side-by-side growing conditions. This is of economic importance as the early market for Granny Smith type apples cannot be taken advantage of with any other cultivar. Also this cultivar can be picked ahead of inclement fall weather, while regular Granny Smith apples are often damaged by fall cold in late October before they can be picked.

I claim:

1. A new and distinct variety of Granny Smith apple tree substantially as herein shown and described, characterized by its compact form and by the early maturing of its fruit with respect to the whiteness of its flesh, the loss of the characteristic (to Granny Smith apples) white spots from its skin, the development of skin of a lighter green color, and, in particular, by early and substantial rise in soluble solids content and early, rapid and substantial drop in total acidity.

* * * * *